(12) United States Patent
Siegal et al.

(10) Patent No.: US 7,727,550 B2
(45) Date of Patent: Jun. 1, 2010

(54) BIOLOGICALLY ACTIVE NATIVE BIOMATRIX COMPOSITION

(75) Inventors: Gene P. Siegal, Birmingham, AL (US); Raj Singh, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 725 days.

(21) Appl. No.: 10/546,506

(22) PCT Filed: Feb. 23, 2004

(86) PCT No.: PCT/US2004/005255

§ 371 (c)(1), (2), (4) Date: Jan. 30, 2007

(87) PCT Pub. No.: WO2004/076631

PCT Pub. Date: Sep. 10, 2004

(65) Prior Publication Data

US 2007/0154552 A1    Jul. 5, 2007

Related U.S. Application Data

(60) Provisional application No. 60/449,303, filed on Feb. 21, 2003.

(51) Int. Cl.
*A61K 9/00* (2006.01)
*C07K 14/00* (2006.01)

(52) U.S. Cl. ............................. 424/484; 514/2; 530/300

(58) Field of Classification Search ........................ None
See application file for complete search history.

(56) References Cited

U.S. PATENT DOCUMENTS

| | | | |
|---|---|---|---|
| 4,829,000 A | | 5/1989 | Kleinman et al. |
| 5,326,357 A | * | 7/1994 | Kandel .................... 623/23.72 |
| 5,354,666 A | | 10/1994 | Danielson et al. |
| 6,179,872 B1 | | 1/2001 | Bell et al. |
| 6,326,019 B1 | * | 12/2001 | Tseng ........................ 424/424 |
| 2002/0177121 A1 | | 11/2002 | Woltering et al. |
| 2002/0197718 A1 | | 12/2002 | Myles et al. |

OTHER PUBLICATIONS

Lallier, T.E. et al. Extracellular Matrix Molecules Improve Periodontal Ligament Cell Adhesion to Anorganic Bone Matrix J. Dental Research (2001) vol. 80 No. 8 p. 1748-1752.
Kleinman H. K. et al., "Basement membrane complexes with biological activity", Biochemistry, 1986, pp. 312-318, vol. 25, No. 2, American Chemical Society, USA.
Friedman J.A. et al., "Biodegradable Polymer Grafts for Surgical Repair of the Injured Spinal Cord", Neurosurgery, Sep. 2002, pp. 742-749, vol. 51, No. 3.
Donovan D. et al., "Comparison of three in vitro human 'angiogenesis' assays with capillaries formed in vivo", Angiogenesis, Apr. 6, 2001, pp. 113-121, vol. 4, Kluwer Academic Publishers, Netherlands.
Siegal G.P. et al., "Development of a novel human extracellular matrix for quantitation of the invasiveness of human cells", Cancer Letters, 1993, pp. 123-132, Elsevier Scientific Publishers Ireland Ltd., Ireland.
Singh R.K. et al., "Tumor Cell Invasion of Basement Membrane In Vitro Is Regulated by Amino Acids", Cancer Investigation, 1996, pp. 6-18, vol. 14, No. 1, Marcel Dekker, Inc.
Hack I. et al., "Reelin is a detachment signal in tangential chain-migration during postnatal neurogenesis", Nature Neurogenesis, Oct. 2002, pp. 939-945, vol. 5, No. 10, Nature Publishing Group.

* cited by examiner

*Primary Examiner*—Anand U Desai
(74) *Attorney, Agent, or Firm*—Bradley Arant Boult Cummings, LLP (57) ABSTRACT

The present disclosure relates to a biologically active biomatrix composition. In one embodiment, the biomatrix composition is derived from human amnions. The biomatrix is termed HuBiogel™. The composition of HuBiogel™ closely mimics naturally occurring basement membrane compositions and is capable of supporting a wide variety of cell types in vitro and in vivo. The HuBiogel™ biomatrix disclosed comprises, in one embodiment, laminin, collagen I, and collagen IV, and may further comprise any combination of the following: entactin, tenascin, fibronectin and proteoglycans. The biomatrix composition is essentially free of endogenous growth factors and proteolytic enzymes. Also described are two- and three-dimensional culture systems and physiological/pathological model systems utilizing the HuBiogel™ compositions. The HuBiogel™ compositions may be modified to contain desired growth stimulants, such as growth factors, polypeptides and organic mall molecules, and may also contain growth inhibitory agents and/or therapeutic agents.

15 Claims, 6 Drawing Sheets

Plastic     Collagen I     HuBiogel     Matrigel

BIOLOGICALLY ACTIVE NATIVE BIOMATRIX COMPOSITION

The present application claims the benefit of U.S. Provisional Patent Application No. 60/449,303, filed Feb. 21, 2003.

FIELD OF THE DISCLOSURE

The present disclosure relates to a biologically active, biomatrix composition derived from human amnions (termed HuBiogel™).

BACKGROUND

The basement membrane (BM) is a continuous structural barrier separating epithelial tissues from adjacent stroma. Major components of the BM include laminin, type I and type IV collagen, entactin, tenascin and proteoglycans, such as heparin sulfate proteoglycans. Since cells are constantly interacting with their extra-cellular environment, the BM is involved in a myriad of processes in vivo. These processes include physiological processes, such as tissue growth and development, bone remodeling, angiogenesis, reproduction, wound healing and neuron regeneration, as well as pathological processes such as tumorigenesis/metastasis (including cellular migration, invasion and angiogenesis), vascular dysfunction, arthritis and aging, and atherosclerosis. In each of these processes, cells interact with and respond to the components of the extra-cellular milieu. As a result, to study these processes in vitro the composition of the extra-cellular milieu (i.e., the BM) must be accurately and reproducibly re-created.

Taking one of the processes discussed above, tumorigenesis/metastasis, the importance of a BM system for in vitro study can be seen. Invasion of the BM is a critical stage in the complex multi-step process of metastasis. The mechanisms controlling tumor invasion through the BM involve multiple morphological and functional events which can be represented as including; (i) tumor cell adherence to the BM via specific cell surface receptors for BM components (such as, but not limited to, the laminin receptor(s); (ii) secretion of BM degrading enzymes (such as, but not limited to, collagenase); and (iii) migration of the tumor cells through BM defects into the circulatory and lymphatic systems, stimulated in part by chemotactic responses.

In order to study the mechanisms of tumor cell invasion, in vitro model systems have been developed. These include both natural and artificial BM systems. The use of naturally occurring BM systems have involved the use of intact BM such as those found in the bladder wall, amnion, lens capsule and chick chorioallantoic membranes. However, when using these naturally occurring BMs in in vitro assays, great care must be taken to ensure that the BM used is intact (i.e., there are no defects in the BM that would allow the test cell to pass through without requiring degradation of the BM). In addition, the thickness of the BM's used in various assays must be uniform. When different thicknesses of BM are used the results of invasion assays will vary dramatically. Therefore, the use of naturally occurring BM in in vitro invasiveness assays is a difficult process subject to significant inter-experiment variation. This makes the result obtained with these assays difficult to compare.

Artificial systems were developed to address these concerns. Initial artificial system utilized composite layers of extracellular matrix proteins that comprise the BM, such as purified rat fibrin, laminin and collagen. Additional artificial BM systems included reconstituted BM-matrices. Matrigel, formulated from reconstituted BM from mouse Engelbreth-Holm-Swarm tumors, is one example. The Matrigel formulation, however, was found not to mimic naturally occurring BM in composition (Matrigel essentially lacks collagen I, an essential protein required for cell-matrix interactions) and to contain significant amounts of growth factors (such as epidermal growth factor, EGF, platelet derived growth factor, PDGF, and fibroblast growth factor, FGF). Matrigel has also been reported to contain collagenase activity. Importantly, the Matrigel composition is both tumorogenic and angiogenic. In many cases, non-transformed cell types display aberrant growth characteristics and invasiveness when cultured in the presence of Matrigel. For example, endothelial cells rapidly form tube like structures when cultured in the presence of Matrigel in the absence of added growth factors or other stimulants, suggesting that growth factors and/or stimulants in the Matrigel composition stimulate this process. In addition, NG108-15 neuroblastoma plus glioma hybrid cells in culture rapidly form long neuritic processes (within 2 hours) in the absence of added growth factors or other stimulants when cultured in the presence of Matrigel, again suggesting endogenous growth factors and/or stimulants in the Matrigel formulation stimulate this process. The presence of growth factors is not surprising since Matrigel was derived from mouse tumor tissues. As a result, formulations such as Matrigel may not be suitable for the determination of invasiveness or other parameters involved in tumor cell invasion since Matrigel provides an artificially stimulated environment as a result of endogenous growth factors and/or other growth stimulants. Although the discussion above has described tumorigenesis/metastasis in detail as one application, the HuBiogel™ biomatrix described herein can also be used to address the deficiencies in other physiological and pathological models, such as those discussed above.

Modifications to the original Matrigel formulation have been attempted, including Matrigel supplemented with collagen and Matrigel containing reduced amounts of growth factors, but even these formulations have failed to provide a reliable reproducible in vitro BM system for study of a variety of physiological and pathological processes. The use of Matrigel has also been hampered by limitations due to its physical properties. For example, the physical form of Matrigel (i.e., gel or liquid) is temperature sensitive, which may impose certain limitations on its use in in vitro assays. Furthermore, it should be noted that Matrigel is derived from mouse BM components raising the possibility that using this composition for the study of human model systems may produce artificial results.

The prior art lacks a defined, biologically active biomatrix derived from human components. The instant disclosure provides such a biomatrix. The biomatrix is termed HuBiogel™.

SUMMARY

Therefore, it is an object of the disclosure to provide a biologically active biomatrix composition (HuBiogel™) capable of supporting growth and differentiation of cell types in vitro and in vivo. It is another object of the disclosure to provide such HuBiogel™ compositions that are free from growth factors and other growth stimulants. A further object of the disclosure is to provide a method of identifying inhibitors and inhibitor candidates of physiological and pathological processes in vitro and in vivo. Another object of the disclosure is to provide a HuBiogel™ composition that is derived from human BM precursors. An additional object of the disclosure is to provide a HuBiogel™ composition that retains similar physical properties over a wide range of use conditions, such as temperature.

It is an additional object of the disclosure to provide a method of preparing HuBiogel™ compositions capable of supporting growth and/or differentiation of a variety of cell types in vitro and in vivo. Further objects include methods to grow cells in two- and three-dimensions using HuBiogel™ compositions.

Further objects of the disclosure include the production of supplemented HuBiogel™ compositions designed for particular needs and uses. It is another object of the disclosure to provide a method for the use of HuBiogel™ in the model systems described herein.

BRIEF DESCRIPTION OF THE DRAWINGS

FIGS. 1A-C illustrate various two-dimensional culture systems for use with the HuBiogel™ compositions described. FIGS. 2A-C illustrate various three-dimensional culture systems for use with the HuBiogel™ compositions described.

FIGS. 3A-C illustrate human umbilical vein endothelial cells grown on two-dimensional HuBiogel™ matrix with or without FGF (15 ng/ml).

FIGS. 4A-D illustrate human umbilical vein endothelial cells grown on three-dimensional HuBiogel™ matrices. FIGS. 4A and B illustrate human umbilical vein endothelial cells cultured using a microbead system, with FIG. 4A showing light microscopy of cellular aggregates and FIG. 4B showing hemotxylin-eosin staining of endothelial monolayers after sectioning of the microbeads. FIGS. 4C and D show human endothelial cells cultured using a three-dimensional bilayer system, with FIG. 4C showing light microscopy of cellular aggregates and FIG. 4D showing hemotxylin-eosin staining of endothelial monolayers after sectioning of the bilayers.

FIGS. 7A and B show a bioassay of angiogenesis using human umbilical vein endothelial cells.

FIGS. 9A and 9B shows photomicrographs (10× objective) of SCI tissue from control group and treatment group animals 3 months after treatment with HuBiogel™ comprising neurospheres plus growth stimulants (NGF+EGF added to HuBiogel™). FIG. 9A shows a view of a longitudinal cut Nissl-stained sections of neural tissue at the site of SCI from an untreated control group animal, while FIG. 9B shows the same view from a treatment animal.

FIGS. 10A-C show photomicrographs (25× objective) of SCI tissues from treatment group animals 3 months after treatment with HuBiogel™ comprising neurospheres plus growth stimulants (NGF+EGF added to HuBiogel™).

FIGS. 11A and 11B show glioma cells cultured on HuBiogel™ containing matrices. FIG. 11A shows a light microscopy image, while FIG. 11B shows an image captured using FITC microscopy.

DETAILED DESCRIPTION

Composition of HuBiogel™

Disclosed is a biologically active biomatrix composition. In one embodiment, the biomatrix is derived from human BM tissue (amnions). In one embodiment, the biomatrix comprises laminin, collagen I, collagen IV. In an alternate embodiment, the matrix may further comprise entactin, and tenascin. In yet an additional alternate embodiment, the biomatrix may further comprise any combination of entactin, and tenascin, fibronectin and proteoglycans, such as heparin sulfate proteoglycans. As used in this disclosure, biologically active means containing the necessary extracellular constituents to maintain the viability and allow the growth of various cell types under in vitro culture conditions. In one embodiment, the extract comprises (by weight) 16-21% laminin, 35-46% collagen I, 19-33% collagen IV, 7.5-14.5% entactin, 3.5 to 7% tenascin, 0 to 2% fibronectin and 0-1.3% proteoglycans. The extract is essentially free of growth factors and proteolytic enzymes (however, growth stimulants may be added as discussed below). This biologically active biomatrix composition is referred to as HuBiogel™.

In one embodiment, HuBiogel is naturally processed, native composition from human starting materials, such as placental amnions. By native composition, it is meant that the components of the HuBiogel composition, when processed from human starting materials, are not individually purified from one another during the processing. In other words, the components of the HuBiogel matrix are simply isolated from the starting material en mass. However, in alternate embodiment, the individual components of the HuBiogel composition may be isolated individually and recombined to for the biomatrix composition.

A variety of processes can be studied using HuBiogel™ as described herein. These include physiological processes, such as tissue growth and development, bone remodeling, angiogenesis, aging, reproduction, as well as pathological processes such as tumorigenesis/invasiveness (including migration and invasion)/angiogenesis, vascular dysfunction, arthritis, and atherosclerosis. HuBiogel may also be used in various restorative procedures.

The HuBiogel™ formulation disclosed is unique in that it maintains the viability of various non-transformed cell types in culture over long periods of time without inducing differentiation. In other words, the HuBiogel™ formulation provides non-transformed cell types an environment where they are not stimulated by exogenous growth factors and/or growth stimulants. This is critical because these cell types can then be subject to stimulation by growth factors and other agents in order to study biological processes that occur in vivo, without interference from growth factors and/or growth stimulants that are present in other biomatrix systems, such as Matrigel. As discussed below, HuBiogel™ compositions are able to support the growth of cells without stimulating differentiation of these cells. Although the specification discusses endothelial cells, in one embodiment human umbilical vein endothelial cells, and neural progenitor cells, in one embodiment neurospheres, in detail the teachings of the present disclosure can be applied to a variety of cell types. One of ordinary skill in the art would be readily able to select a cell type of interest and perform routine cell culture manipulations to observe that HuBiogel™ promotes growth and viability of non-transformed cell types without differentiation. Such experiments could be accomplished in less than a week and would not require undue burden or experimentation. In human umbilical vein endothelial cells, differentiation (as measured by sprout/capillary formation) only occurred in the presence of specific growth factors, such as FGF, added to the HuBiogel™ formulation. Similar results were obtained from neurospheres.

Using the HuBiogel™ compositions disclosed, the molecular mechanisms of a variety of physiological and pathological processes can be study in vitro. In addition, therapeutic agents that inhibit or stimulate this process can be identified and their mechanisms studied. Previous BM compositions were unable to provide such an environment. For example, when non-transformed cell were cultured on Matrigel, endogenous growth factors present were found to stimulate the cellular differentiation in a rapid manner, eliminating the possibility of using this BM system to study analyze critical mechanisms that occur in vivo.

Figure 10:
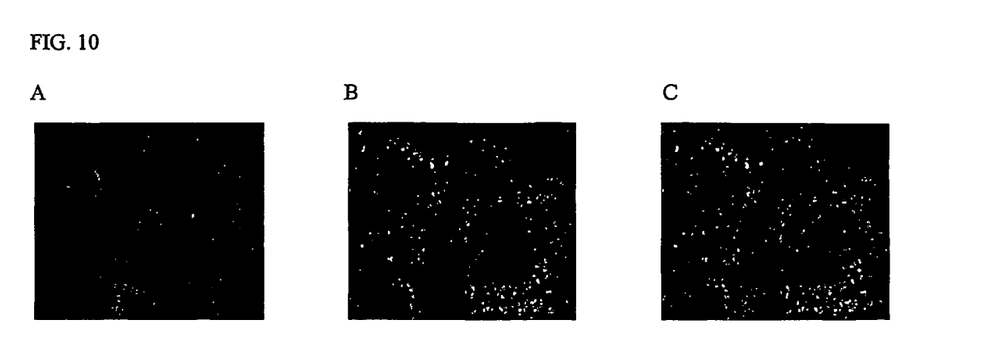
FIG. 10A, shows collagen I specific immunohistochemistry revealing the type I collagen (the major component of HuBiogel™) organization.
FIG. 10B shows the distribution of implanted cells (labeled with CFDA-SE Cell Tracker kit prior to implantation).
In FIG. 10C, the fused image shows the relationship of the implanted cells and the type I collagen biomatrix architecture at the site of SCI.

For transformed cell types (which may undergo cellular growth and differentiation stimulated in an autocrine or paracrine manner), HuBiogel™ provides a natural environment to study the neoplastic events as they occur in vivo. As discussed below, human tumor cells cultured on HuBiogel™ matrices attached to the HuBiogel™ matrix and initiated time dependent migration and invasion processes. This process occurred in a temporally isolated manner over a 72 hour period. Using the HuBiogel™ system, the events involved in the migration and invasion process can be temporally isolated and studied individually to determine the molecular mechanisms involved in each stage of the process. In addition, additional agents can be added to inhibit or stimulate these processes in a defined manner. Previous BM systems could not offer this advantage. For example, using a Matrigel matrix, the entire migration and invasion process occurred in a 5 hour time window (described in U.S. Pat. No. 4,829,000, Example 2 and FIG. 10). This has been postulated to be due to the added growth factor and/or other growth stimulates present in the Matrigel composition. Furthermore, because of this background of endogenous growth factors and/or growth stimulants, it is difficult to determine the effect of individual stimulators and inhibitors of the biochemical process at work in the migration and invasion steps.

A comparison of the composition of HuBiogel™ (derived from non-transformed human tissue) and Matrigel (derived from mouse EHS tumor tissue) is given in Table. 1. In addition, a comparison of the physical properties of selected biomatrix formulations is given in Table 2. As can be seen, the composition of the HuBiogel™ and Matrigel differs greatly. For example, the major component of Matrigel is laminin, being present at a concentration of greater than 50% of the total weight. In contrast, the major component by weight of the HuBiogel™ formulation is collagen I, which is lacking to a significant degree in Matrigel. In addition to collagen I, Matrigel also lacks the ECM components tenascin and fibronectin. Importantly, Matrigel contains significant concentrations of EGF, TGF-$\beta$, bFGF, PDGF and VEGF as well as proteolytic enzymes such as collagenases. Such growth factors and proteolytic enzymes are not detectable in the HuBiogel™ formulations.

These differences in composition are also reflected in different properties of the various biomatrix systems. HuBiogel™ is a semi-gel derived from natural ECM components. The semi-gel form is stable over a wide range of temperatures (from 4 degrees to 37 degrees C.). As a result, HuBiogel™ forms coatings and structures (2 and 3-dimensional) of uniform characteristics which exhibit flexibility. Matrigel can exist in a liquid or a gel form and is derived from mouse tumor tissues. The form of Matrigel is temperature dependent. As a result, coatings and structures formed with Matrigel may exhibit non-uniform characteristics (referred to in the art as a "leaky" coating, for example). Critically, HuBiogel™ provides an environment for unstimulated cell growth (without activation by growth stimulants) and allows the creation of defined and controlled environments where specific processes can be modulated and studied in a controlled manner free of background caused by endogenous factors. For example, using the HuBiogel™ system, a cell type (for example, endothelial cells) could be cultured in a manner such that the cells are maintained in a viable state and not subject to differentiation. Furthermore, the cells may be stimulated to undergo growth of differentiation or other physiological processes by the addition of appropriate growth stimulators, such as growth factors (including, but not limited to, FGF), polypeptides, cytokines or organic small molecules, or by the addition of growth inhibitors. Modulators (inhibitors and stimulators) of this process could then be analyzed in order to isolate potential therapeutic compounds. Matrigel on the other hand contains endogenous growth factors and/or growth stimulants that preclude the ability to maintain cells in a viable state without inducing differentiation or accelerated growth. As a result of this activation, it is difficult, if not impossible, to study the effects of single factors or combinations of factors on specific processes and to identify modulators of those processes using the Matrigel system.

The basic HuBiogel™ composition disclosed can be modified in a variety of ways. HuBiogel™ compositions can be modified by adding one or more desired growth stimulants, such as growth factor(s), cytokines or polypeptides, at desired concentration ranges. Growth inhibitory compositions may also be added, as well as potential therapeutic compounds. Growth stimulants may be added singly, or in combinations. Growth factors that may be added include, but are not limited to, EGF, PDGF, FGF, Insulin, insulin-like growth factors, vascular endothelial growth factor (VEGF), nerve growth factor (NGF), kerotinocyte growth factor (KGF), hepatocyte growth factor (HGF), brain-derived neurotropic factor (BDNF), neurotropin-3 and -4, CNF (Ciliary neurotrophic factor), glial growth factor (GGF), glial maturation factor (GMF) glial-derived neurotropic factor (GDNF), other growth factors disclosed herein and other growth factors known in the art. The selection of the target cell type may influence the selection of growth stimulatory compound. These factor enriched HuBiogel™ formulations may also be engineered to release the factor(s) in a controlled manner over time. Bio-peptides may also be added to HuBiogel™ compositions. The specific peptides may be matrix related peptides (such as peptides being tested to block adhesion of tumor cells to the tumor matrix) or growth related peptides (such as growth factors, hormones or cytokines). Examples of peptides include, but are not limited to, adhesion peptides, laminin or thrombospontin related peptides endostatin and angiostatin. Other matrix proteins may also be added to the HuBiogel™ composition. For example, ECM components such as, but not limited to, fibrin, fibronectin, vitronectin, collagen, II, III, V-VIII, and osteopontin may be added. The development of alternate HuBiogel™ formulations will allow the development of HuBiogel™ formulations that contain both positive and negative regulators of a desired process, such as growth, differentiation, or invasion.

Preparation of HuBiogel™

HuBiogel™ can be prepared in large scale batches with superior reproducibility of components. The large scale preparation procedure is designed to provide large quantities of HuBiogel™ compositions with low batch to batch variation and improved reproducibility. In addition, the protocol has been designed to provide convenient break points for an orderly and efficient production process. All steps are performed at 4 degree C. (or on ice) maintaining sterile conditions and techniques. The entire protocol requires 5-7 days. All solutions are made with autoclaved Q-water and sterilized using 0.2 μm filters.

Step-1 Processing of amnions: After separating amnions from normal placentas (15-20 placentas, grossly unremarkable, collected daily between 6-24 hrs of vaginal delivery time), the inside epithelial surfaces (rough side) are marked with tweezers. Intact amnions are cleaned using wet cotton gauze to remove blood clots. All amnions are further rinsed/cleaned using wet-gauzes during the five sequential washing steps (5-10 min each): two washes with PBS (500 ml/wash); one wash with 10.5% ammonium hydroxide/PBS solution (50 ml/amnion) to remove all cellular materials; and two final washes with PBS to remove all contaminants. Amnions are soaked dry, weighed and stored frozen at −20 degrees C.

Step-2 Homogenization and Solubilization of Amnions: Frozen amnions are thawed quickly in a 37 degrees C. water bath, immersed in a culture-tray containing ice-cold 0.5 M acetic acid solution and cut into small pieces. Final volume is adjusted to 5 ml of 0.5 M acetic acid per gram (wet wt) of tissue. Amnions are homogenized on ice using Polytron device (P20 generator) at 4000-6000 rpm for 2-3 min with cooling intervals of 5 min. Resultant homogenate should look uniform and without any tissue clumps or pieces (this step may take 20-30 minutes). The pH of homogenate is slowly adjusted to 2.0 using first 1-2 N HCl followed by 0.1 N HCl. (Note: avoid any major volume increase or precipitation during this pH adjustment step). A limited digestion with Pepsin (Sigma Co.) is performed by slowly adding solid pepsin powder into solution (8.6 mg per gram of amnions). Mixture is incubated in cold room for 32-36 hrs with constant but gentle stirring. At this step, the solubilized solution should appear homogeneous.

Step-3 Salt extraction #1 and enzyme inactivation: Solubilized (amnion) solution is centrifuged at 4,600 rpm (Beckman J-14 rotor) for 18 min at 4 degrees C. Supernatant is removed and the pH of supernatant is raised to pH to 7.8 first using 5N NaOH (up to pH 6.0) and then with 0.1 N NaOH. Next the HuBiogel™ solution is slowly adjusted to 50 mM Tris (base) and 4M NaCl, avoiding any major volume change and precipitation during this enzyme inactivation step. This is accomplished by combining solid Tris+NaCl and adding small amounts with constant stirring. Note the final volume and incubate HuBiogel™ extract in cold room for 18-20 hrs with gentle stirring. If the pellet is fluffy and big after any centrifugation step, it is extracted with a combination of pepsin and collagenase I mixture (1-2 mg/ml) and incubated 6-8 hrs to fully recover remaining collagens. After centrifugation as above, supernatants are combined. If white precipitate or partitioning occurs, solution pH can be readjusted to 2.0 with HCl and Step-3 is repeated as above.

Step-4 Salt extraction #2: HuBiogel™ extract is centrifuged at 12,000 rpm (Beckman rotor) for 30 min. The pellet is resuspended in one-half of the measured volume with 0.5 M acetic acid using a rapid low-speed homogenization (1,000 rpm/30 sec×6). Raise the pH of solution to 7.8 with NaOH and perform solid Tris/NaCl addition and extraction same as in Step-3. However, solution is stirred only for 2-3 hrs at 4 C. (not overnight as in step-3). Measure the final volume and centrifuge again at 12,000 rpm for 30 min. Discard the supernatant and resuspend the pellet in one-half of the measured volume with dialysis solution (5 mM acetic acid, 5 mM KCl and 135 mM NaCl) and stir gently overnight in cold room.

Step-5 Dialysis, Sterilization and Concentration: HuBiogel™ solution is placed in dialysis bags (45 mm with 12,000 MW cut-off size) and equilibrated against dialysis solution (100 times V/V with three 6-hour changes) for a total of 24 hrs in cold room. To maintain sterility of HuBiogel™, 5-10 ml of chloroform is placed at the bottom of dialysis vessel during the last change. To avoid any precipitation dialysis bags are mixed every few hrs and HuBiogel™ solution is divided into 150-200 ml size dialysis bags. Finally, HuBiogel™ solution is concentrated by ultrafiltration using Amicon stirred cell (400 ml) and 12K cut-off filter membranes under nitrogen pressure (20-30 psi). Highly concentrated HuBiogel™ stocks (3-8 mg/ml) are obtained by monitoring concentration speed and time.

Step-6 Storage of HuBiogel™ Stocks: Stocks of HuBiogel™ are pooled and/or stored at 4 degrees C. for short-term (2-4 wks) storage and at —20 degrees C. for long-term (2-4 months) storage. HuBiogel™ stocks are neutralized with PBS and HEPES (pH 8.5) using a dilution ratio of 1:1:0.5 (V/V), respectively. In addition, HuBiogel™ stocks can also be conditioned and stored in defined media (sterile HBSS or DMEM) via dialysis prior to bioassays.

The above description of the HuBiogel™ preparation process is provided to allow the reader to understand the steps involved in the preparation process. Alterations to the process that would be obvious to one of skill in the art are considered to be covered by the method presented.

Analysis of HuBiogel™ Components

Total protein content of HuBiogel™ preparations is measured by the BCA protein assay (Pierce, Ill.). SDS-PAGE of HuBiogel™ samples is carried out on 4-10% gradient gels which are subjected to Coomassie blue staining or Western blot analysis. Molecular weights of proteins are determined using protein standards and confirmed by immunoblots of parallel gels. Quantitation of proteins including laminin, types I and IV collagen, tenascin, proteoglycans and entactin are determined by slot blot techniques using monospecific antibodies (Chemicon, Neomarkers, Southern Biotech) to each protein. Immunoblots are probed using the HRP conjugate kit (BioRad) and quantitated by computer-aided digital densitometry analysis. The amounts of various growth factors (such as, but not limited to, EGF, TGF, VEGF, FGF, IGF) are validated by standard ELISA kits or flourometric methods. Protease activity is determined by gelatin zymography on SDS-PAGE. Potential contaminants (virus, fungi and bacteria) are analyzed using standard microbiology test kits.

Two- and Three-Dimensional Methods for Cell Culture Utilizing HuBiogel™

HuBiogel™ may be incorporated into a variety of cell culture, implant and biometric plug systems. This is feasible since HuBiogel™ retains its semi-gel state at 4 and 37 degrees C. Target cell types may be encapsulated in a desired HuBiogel™ formulation for in vivo applications. Applications include tissue repair, tissue/organ regeneration, wound healing/repair and bioengineering applications.

Figure 1A:
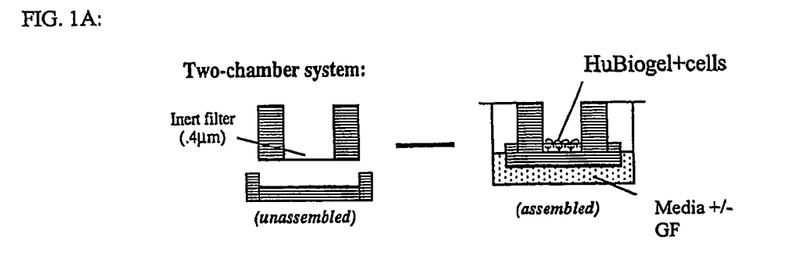
FIG. 1A shows a two-chamber system.
Figure 1B:
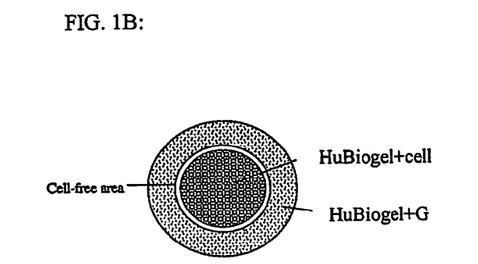
FIG. 1B shows a disc system and FIG. 1C shows a bilayer system
Figure 1C:
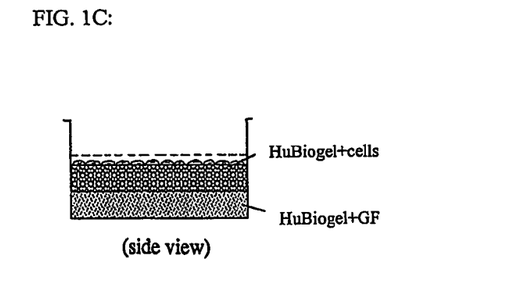

A variety of culture system can be used with the HuBiogel™ system. These include two- and three-dimensional systems in both static and rotating environments. Embodiments of the two-dimensional systems are shown in FIG. 1 and embodiments of the three-dimensional systems are shown in FIG. 2. FIG. 1 discloses a two chamber system (FIG. 1A), a disc system (FIG. 1B) and a bilayer system (FIG. 1C). Referring to the two chamber system, an insert filter (of desired porosity, in this embodiment 4 μm) is placed in the top chamber. These systems may be re-usable or disposable. In one embodiment, a layer of HuBiogel™ is layered on top of the disk. The concentration of HuBiogel™ may as desired for experimental purposes. For example, 75 μg of HuBiogel™ may be layered on the filter. Other concentration ranges may be used as desired. These concentrations may be empirically determined by one of ordinary skill in the art without undue experimentation. For example, for invasion assays the thickness of the HuBiogel™ matrix will impact the number of cells invading the matrix, with concentrations suitable for a particular cell line under particular growth conditions being optimized for each experiment. Concentration ranges from 25 to 200 μg/filter have been used by Applicants. Desired media is placed in the top chamber along with the cell type to be tested (such as endothelial cells). The media may be supplemented with growth stimulatory agents, such as growth factors and polypeptides, or therapeutic compounds as desired, as well as commonly used media supplements. A variety of cell types may be used as discussed above, with endothelial cells being stated for exemplary purposes only. The bottom of the chamber contains media and or a HuBiogel™/media combination and may be supplemented as described. In this embodiment, when growth factors or other agents are added to the HuBiogel™ or HuBiogel™/media combination, these growth factors or other agents may diffuse within the chamber to interact with the cells being cultured. The concentration of HuBiogel™ layered on the disk may be different from the HuBiogel™ concentration employed in the bottom of the system. The HuBiogel™ may be supplemented with growth factors or other stimulants, polypeptides and/or therapeutic compounds as discussed above.

A two-dimensional disc system is illustrated in FIG. 1B. The disk system comprises a solid support on which a layer of HuBiogel™ matrix is deposited along with the desired cell type (such as endothelial cells). The HuBiogel™ matrix is contained within a defined area by a ring or another suitable containment means to create a cell free area. Media or HuBiogel™/media combinations are placed around the HuBiogel™ matrix. The media may be supplemented with growth stimulatory agents, such as growth factors and polypeptides, or therapeutic compounds as desired, as well as commonly used media supplements. Various HuBiogel™ concentrations may be used and the HuBiogel™ may be supplemented with growth factors or other stimulants, polypeptides or therapeutic compounds as discussed above. In this embodiment, when growth factors or other agents are added to the HuBiogel™ layer surrounding the cells, these growth factors or other agents may diffuse to interact with the cells being cultured. As above, the HuBiogel™ concentrations that are in contact with the cells may be different from the HuBiogel™ concentrations that surround the cells.

A bilayer HuBiogel™ system is illustrated in FIG. 1C. In this system a base layer of HuBiogel™ (which may be supplemented as described above) supports a layer of HuBiogel™ onto which a desired cell type (such as endothelial cells) is placed. The desired media is placed on top of the cells and the cells are incubated as appropriate. The media may be supplemented with growth factors, peptides or therapeutic compounds as desired, as well as commonly used media supplements. In this embodiment, when growth factors or other agents are added to the base HuBiogel™ layer, these growth factors or other agents may diffuse upward to interact with the cells being cultured. Various HuBiogel™ concentrations may be used as discussed above. As above, the HuBiogel™ concentrations that are in contact with the cells may be different from the HuBiogel™ concentrations that support the upper HuBiogel™ layer.

Three-dimensional culture systems are shown in FIG. 2. These three-dimensional systems may be used with the rotating cell culture system as described below. FIG. 2A shows a microbead system where HuBiogel™ is coated on the surface of a microbeads (any size bead may be used, but in this embodiment beads 10-20 μm in size are used). HuBiogel™ concentrations may be selected as desired depending on experimental parameters as discussed above, but Applicants have used 5-25 μl of 5 mg/ml HuBiogel™ (25 to 125 μg) in these embodiments. The cell type to be tested is placed in contact with the HuBiogel™ coating the microbeads and allowed to attach. As discussed above, a variety of cell types may be used with endothelial cells being shown for exemplary purposes only. The microbeads are then placed in an appropriate culture system, such as the rotating cell culture system with desired media formulations. The HuBiogel™ and/or media may be supplemented with growth factors or other stimulants, peptides and/or therapeutic compounds as discussed above.

Figure 2A:
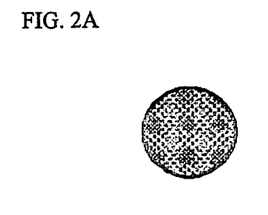
FIG. 2A shows a microbead system.
Figure 2B:
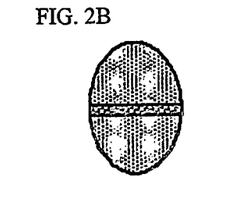
FIG. 2B shows a bilayer system and FIG. 2C shows a microvessel system.

A three-dimensional bilayer system is shown in FIG. 2B. In this system, cells to be studied are placed in between two three-dimensional semi-spherical constructs of HuBiogel™ as shown. The cells may be placed directly in contact with the HuBiogel™ or supported by a filter or other support means. The HuBiogel™ may be supplemented with growth factors or other stimulants, peptides and/or therapeutic compounds as discussed above. The HuBiogel™ concentration may be as desired depending on experimental parameters, but for the embodiment illustrated the HuBiogel™ bilayer system is comprised of 5 mg/ml HuBiogel™. The physical properties of HuBiogel™ are such that the form of the bilayer system is maintained under experimental conditions, such as incubation in liquid media at temperatures from 4 to 37 degrees C. A rotary cell culture system may be used as described herein.

Figure 2C:
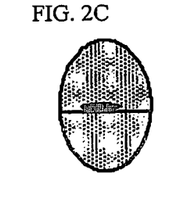
Figure 2D:
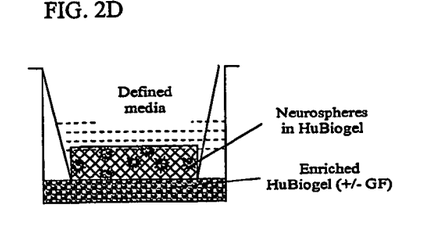
FIG. 2D shows an embodiment of the scaffold system.

A three-dimensional microvessel system is illustrated in FIG. 2C. In this system the microvessel is completely implanted in the HuBiogel™ three-dimensional support. The microvessel may contain the cell type to be cultured. The HuBiogel™ concentration may be as desired depending on experimental parameters, but for the embodiment illustrated the HuBiogel™ has bilayer system is comprised of 5 mg/ml HuBiogel™. The physical properties of HuBiogel™ are such that the form of the microvessel system is maintained under experimental conditions, such as incubation in liquid media at temperatures from 4 to 37 degrees C. The HuBiogel™ may be supplemented with growth factors or other stimulants, peptides and/or therapeutic compounds as discussed above. A rotary cell culture system may be used as described herein.

Tumor Invasion Assay System

Invasion chambers were used to study cellular invasion by transformed cells. Filters (in one embodiment, polycarbonate filters, 8 μm pore size) were sandwiched between the top and bottom chambers. HuBiogel™ solution of the desired concentration (4-8 mg/ml) were diluted in PBS and 1 M HEPES, pH. 5.5 (ratio of 1:1:0.5). HuBiogel™ at the desired concentration, in this example (75 μgs/filter) was coated onto the filter and incubated overnight at room temperature in a sterile hood. Filters were re-hydrated in serum free media. It was observed that the HuBiogel™ coating was of uniform thickness after re-hydration. Cells ($5\times10^4$) are placed on the HuBiogel™-coated filter in desired media plus BSA. The cells may be radioactively labeled by standard protocols if desired. Lower chambers were filled with media, either with or without factors to stimulate tumor invasion. Cells were allowed to attach for 24 hours, after which the media in the top chamber was removed and replaced with BSA-free media and incubation continued for 48 hours at 37 degrees C.

Cells traversing the HuBiogel™ coated filter were determined by collection on a filter placed beneath the coated filter and counting the cells or by scintillation counting (if cells were radioactively labeled).

After 72 hours HT-1080 cells showed a 12-15% invasion rate. The invasiveness of HT-1080 cells was 8-10-fold greater than the invasiveness of human foreskin fibroblast cells or human endometrial stromal cells (both non-transformed cells) which was determined to be less than 2%. It was observed that HT-1080 cells attached to the HuBiogel™ matrix starting a 2 hours and migration towards the underlying filter chamber was distinctly evident at 24-48 hours. At 72 hours the invasive cells showed cell spreading around the filter pores, both at the interphase with the HuBiogel™ border and on the underside of the filter as well. The growth of transformed cell types in a manner such that discrete events can be isolated temporally for study and observation is referred to herein as "controlled growth" or "growth in a controlled manner".

When cells that migrated through the HuBiogel™ matrix were collected from the lower chamber and tested again for invasiveness/metastatic potential, a 2-3 fold increase in invasiveness was observed as compared to the parental cells.

This basic protocol may be modified by using HuBiogel™ compositions containing growth stimulants, such as growth factors or peptides, or therapeutic compounds or other agents as has been described. In addition, the media in the top and/or bottom chambers can contain such agents as well. The assay may therefore be used to assess the invasiveness/metastatic potential of cells under any set of conditions described herein. In addition, therapeutic compounds that modulate this invasiveness/metastatic potential can be identified and studied. As compared to similar experiments conducted with Matrigel, the use of HuBiogel™ provides a model system in which the events involved in invasion and metastasis are temporally separated and studied individually.

Growth and Differentiation of Human Umbilical Vascular Endothelial Cells on Two-Dimensional HuBiogel™ Matrix Tumor angiogenesis, the formation of new blood vessels during malignancy, critically depends on host cell-matrix interactions. Both matrix proteins (collagen, laminin, fibronectin) and growth factors (FGF, VEGF), which may be tumor derived, act as potent angiogenic stimuli and regulate angiogenesis process. This cellular angiogenesis morphogenic cascade involves: (i) endothelial cell migration; (ii) proliferation; and (iii) differentiation to form new capillaries in response to locally-produced angiogenic factors. Sprout formation of activated endothelial cells is an early stage of angiogenesis after which cell differentiation occurs to form tubular capillary structures.

Figure 3A:
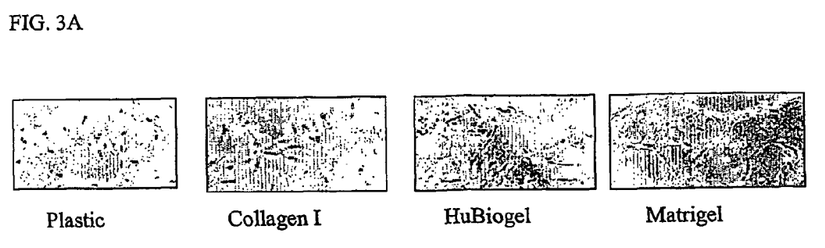
FIG. 3A shows human umbilical vein endothelial cells cultured on a variety of substrates as indicated in the absence of added growth factors or growth stimulants.
Figure 3B:
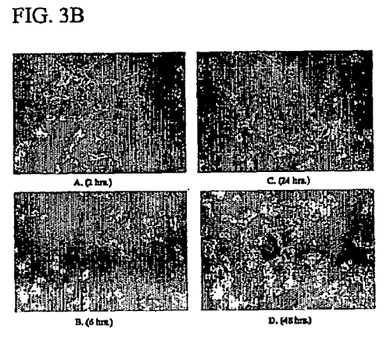
FIG. 3B shows human umbilical vein endothelial cells cultured on the HuBiogel™ matrix in the presence and absence of 15 ng/ml FGF over a 48 hour period.
Figure 3C:
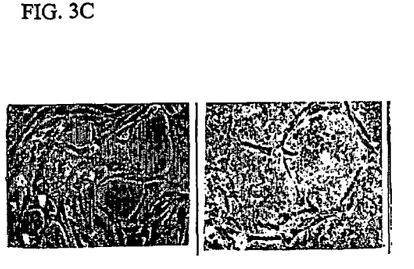
FIG. 3C shows the formation of tubule and capillary-like structures after 7 days growth on HuBiogel™ in the presence of 15 ng/ml FGF.

FIG. 3A show the results of culturing human umbilical vascular endothelial cells (HUVEC, approximately $1\times10^4$ in one embodiment) on several defined biomatrix environments (plastic, natural collagen I rich-biomatrix, HuBiogel™ and Matrigel) without added angiogenic stimuli. The specific morphological changes in the monolayer HUVEC cultures was examined after 72 hrs incubation on each biomatrix environment. HUVECs cultured on plastic or purified collagen I grew poorly (<60% viability). FIG. 3A shows that cells plated on the HuBiogel™ biomatrix environment grew and proliferated normally (with <15% sprouting). In contrast, cells cultured on the Matrigel biomatrix environment rapidly differentiated into tubule-like structures. Interestingly, HUVECs can be grown and maintained (without differentiation) up to at least 15 days on HuBiogel™ formulation with high viability (>90%). While a rapid differentiation or angiogenesis was noted with Matrigel (even growth factor reduced Matrigel) formulations, endothelial cells do not form tubule-like structures indicative of differentiation under the defined, growth factor free environment of HuBiogel™. FIG. 3B shows the results of adding purified angiogenic factors to the HuBiogel™ formulation. Enrichment of HuBiogel™ with FGF (15 ng/ml) triggers a time and dose dependent rapid formation of tubule-like structures (FIG. 3B). Tubular capillary formation is confirmed by cross-sectional electron microscopy showing distinct lumen. FIG. 3(c) shows the formation of tubule and capillary-like structures after 7 days growth on HuBiogel™ in the presence of 15 ng/ml FGF. Thus, HuBiogel™ supports normal endothelial cell growth and proliferation but promotes cell differentiation only in the presence of defined angiogenic factors As a result, HuBiogel™ is superior to Matrigel and collagen I matrices for delineating the functional stages of angiogenesis process.

Functional Model of Angiogenesis and Tumorigenesis Using Three-Dimensional HuBiogel™ Matrix There is a need for developing angiogenesis and tumorigenesis model which mimics the in vivo biology of tumors. At present, tumor studies mostly utilize monolayer cell cultures and animal-derived biomatrix systems. The commonly used Matrigel and collagen models exhibit major compositional and biological limitations, as discussed previously herein. Moreover, no well defined functional model is available for examining the important stages of angiogenesis and tumorigenesis in humans. Utilizing HuBiogel™, such a system has been developed by the Applicants. The HuBiogel™-based bioassay allows the analysis of discrete cellular and molecular events of tumor growth and progression in vitro. The model may be used for a variety of applications, including, but not limited to, the study of cancer biology, drug discovery and therapeutic intervention of physiologically relevant pathways involved in angiogenesis and tumorigenesis (including invasion and metastatic potential).

HuBiogel™ is a biologically active, human biomatrix which mimics a controlled microenvironment for both cell-cell and cell-matrix interactions. By using defined formulations of the HuBiogel™ biomatrix and multicellular tumor spheroid coculture systems, a clinically-relevant three-dimensional functional model of angiogenesis and tumorigenesis has been established. This new functional bioassay is useful for studying both early and late stages of tumorigenesis cascade including cell proliferation, invasion and angiogenesis events, allowing the identification of specific positive or negative regulators of tumor growth/progression, and in parallel permit analysis of malignant (invasive, angiogenic) behavior of target cells removed from primary tumors.

HuBiogel™ formulations may also be employed in three-dimensional cell culture systems. The development of three-dimensional culture systems with defined stromal and basement membrane components is critical to the physiologically relevant study and analysis of the mechanisms of development for a variety of tissues. Both three dimensional microbead and disc-type (disks with 10-200 um pore size) biomatrix formulations have been developed using HuBiogel™ and custom-made Lucite microwell plates.

Figure 4:
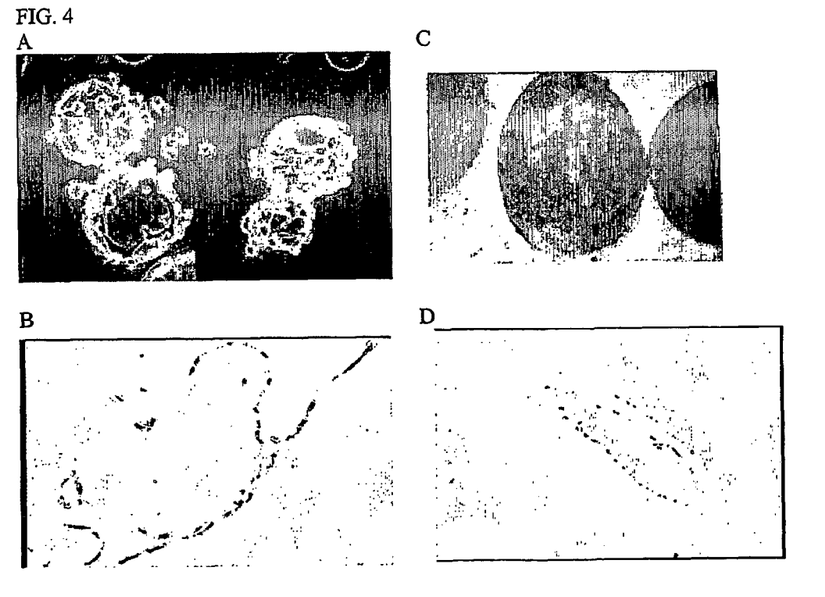

In one example of a three-dimensional culture system, HUVECs were grown under standard conditions in a rotating cell culture system (Synthecon, Austin Tex.; methods for using such systems can be found in U.S. Pat. Nos. 4,998,632, 5,026,650 and 5,115,034). The rotating cell culture system provides minimized mechanical stresses, such as fluid shear stress and surface tension stress, increased 3-D freedom for cell and substrate spatial orientation and increased maintenance of tissue components in a natural spatial organization during the culture process. HUVECs were grown on HuBiogel™ coated microbeads (in one embodiment, bead diameter were 10-200 μm, and microbeads were coated with 5-25 μl of 5 mg/ml HuBiogel™ formulation) (FIGS. 4A and B) or encapsulated within HuBiogel™ bilayers (5 mg/ml HuBiogel™) (FIGS. 4C and D) as described. The endothelial cells were cultured 36 to 48 hours and cell morphology was examined. FIGS. 4A and 4C shows light microscopy images of the cellular aggregates of HUVECs grown on microbeads and encapsulated within bilayer systems, respectively. Histologic examination of HUVECs revealed active cell growth, typical cellular organization and formation of multicellular structures FIGS. 4B and 4D shows correct endothelial cell morphology and monolayer formation after hemotoxylin and eosin staining (cross sections) of the cells grown on microbeads and encapsulated within bilayers, respectively.

A recent study has shown that spheroids composed of solid stratified cells cocultured with stromal elements enhance cellular organization. Thus, the collagen-rich milieu of HuBiogel™ offers a suitable defined biomatrix environment for the proposed in vitro tumorigenesis studies. The use of HuBiogel™ in three dimensional culture systems will allow the development and optimization of a three-dimensional cell-matrix model for evaluating the key stages of tumor invasion and angiogenesis process. Currently available co-culture models utilize animal-derived biomatrix and biopolymer scaffolds and suffer from the disadvantages discussed previously herein. The use of HuBiogel™ three-dimensional coculture systems provides a system where cell-cell interactions and cell-matrix interactions with both basement membrane and stromal elements are preserved. As a result, multi-cellular organization is preserved providing a physiological model to study a variety of processes, including, but not limited to, tumorigenesis and angiogenesis.

Figure 5:
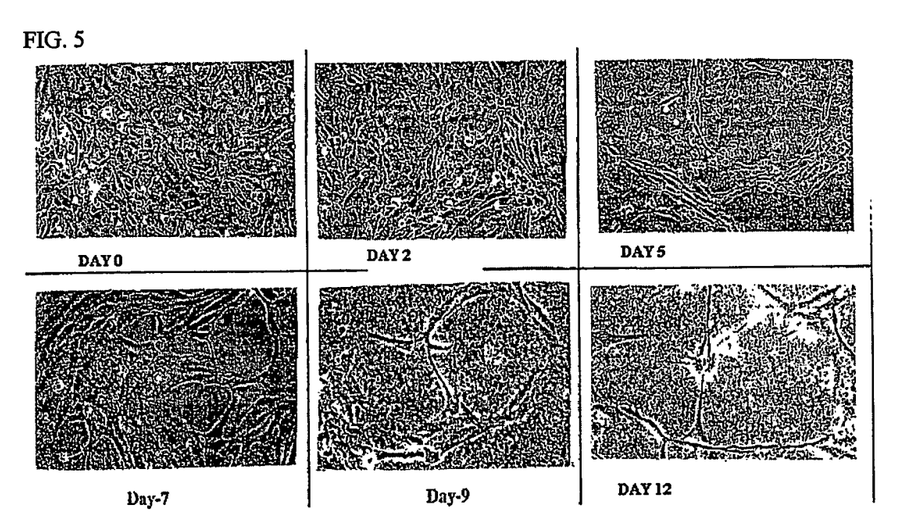
FIG. 5 shows growth factor induced human umbilical vein endothelial cell activation, migration and differentiation in the presence of FGF (15 ng/ml) using the three-dimensional HuBiogel™ disc culture system.

FIG. 5 shows growth factor induced HUVEC migration and differentiation using the three-dimensional HuBiogel™ disc culture system (in one embodiment, 5 mg/ml HuBiogel™ was used with a disc having a 50 um pore size). Endothelial cells were cultured under standard conditions. On day 0, FGF (60 ng/ml) was added to the culture and incubation continued. At the indicated times, cell morphology was examined and documented. As can be seen, FGF induced a time dependent series of cellular activation, migration and differentiation steps. As can be seen, from day 0 through day 5 the cells are involved in the activation and migration steps. There is no differentiation of the cells until the day 5-day 7 time period. After day 7, obvious differentiation as indicated by sprout formation/capillary formation can be seen. As was seen in FIG. 3A, there was no activation, migration or differentiation in the absence of FGF after a 7-day period. Such a temporally discrete timing of the activation migration and differentiation steps make the use of this system ideal for studying the biochemical mechanisms involved in each step, as well as isolating potential inhibitors of the mechanisms identified. This time dependent, temporally isolated sequence of events is in contrast to that seen with Matrigel, where differentiation events occur rapidly in the absence of added growth factors and/or growth stimulants.

Figure 6:
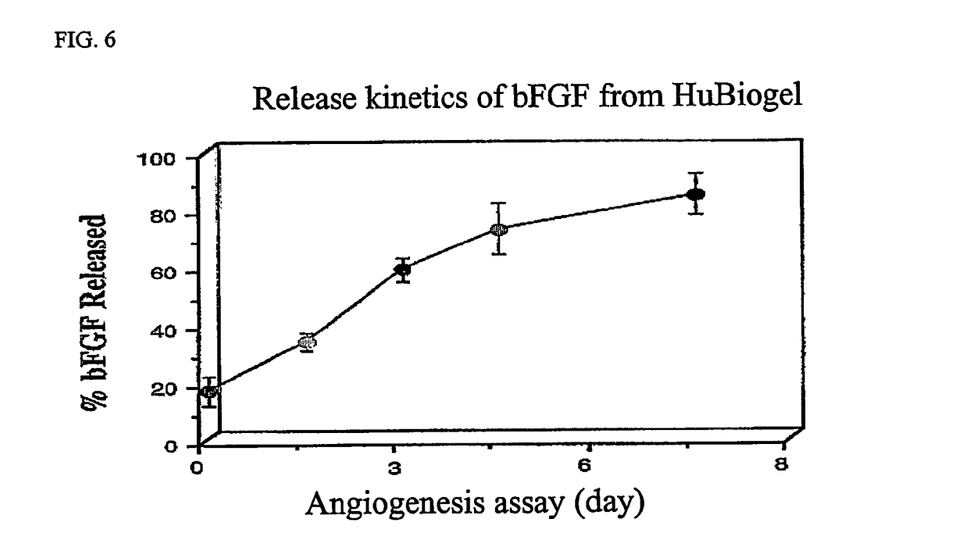
FIG. 6 shows the release kinetics of bFGF from the basic HuBiogel™ formulation.

As shown in FIG. 6, HuBiogel™ is ideally suited to use in three-dimensional culture systems. FIG. 6 shows the release kinetics of bFGF (60ng/ml) released from the basic HuBiogel™ formulation (5 mg/ml). bFGF is consistently released throughout the course of the experiment. These release kinetics are also useful for implant studies, tissue repair/regeneration, wound healing and other in vivo applications.

Figure 7:
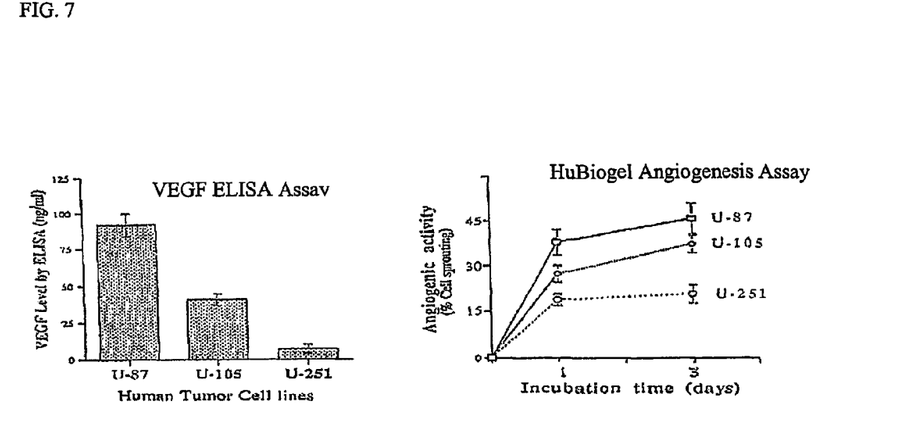
FIG. 7A shows the VEGF concentration in conditioned media produced by three human tumor cell lines.
FIG. 7B shows the effect of the VEGF-conditioned media on human umbilical vein endothelial cell differentiation when the cells are grown in the presence of a HuBiogel™ matrix.

We have also studied the modulation of angiogenesis by human tumor cell-secreted angiogenic factors (i.e. a complex biologic milieu). HUVECs were grown on a HuBiogel™ three-dimensional disc culture system (in one embodiment, 5 mg/ml HuBiogel™ was used with a disc having a 50 um pore size) in the presence of conditioned media from thee human glioma cell lines (U-87, U-105 and U-251) producing different levels of the potent angiogenic factor VEGF were tested. FIG. 7A shows the VEGF concentration in ng/ml (as determined by ELISA) secreted into the media by each cell type. The angiogenic activity (determined as a percentage of cell sprouting) of HUVECs was measured at day 1 and day 3 (FIG. 7B). As can be seen, the angiogenic activity was found to positively correlate to the level of VEGF secreted by each tumor cell (FIG. 7A). As U-87 tumor cells secreted the most VEGF, HUVECs exposed to U-87 conditioned media exhibited the most angiogenesis. This result shows that as a result of the normal host matrix environment in HuBiogel™, the discrete cellular and molecular events of tumorigenesis and angiogenesis can be dissected using HuBiogel™ as a "controllable" culture model, in both 2-dimensional and three-dimensional cell culture systems.

Functional Model of Neurogenesis Using Three-Dimensional HuBiogel™ Matrix

One of the continuing unmet needs in the medical field is the repair and reconstruction of damaged tissues. In particular, spinal cord injuries (SCI) are particularly devastating as it impairs the mobility and freedom of the affected individuals. SCI affects approximately 12,000 Americans each year. SCI pathology is complicated and involves damage to axons, loss of neurons and glia and demyelination. Previous strategies to enhance functional recovery involved use of blocking agents to overcome local inhibitory cues, axonal re-growth by implanted neural cells, Schwann cells and/or olfactory cells, delivery of neurotrophic factors via gene therapy, and transplantation of fetal tissue and cell-matrix scaffolds.

Recent evidence supports the existence of stem cells that are capable of repairing injured tissue in adult brain and spinal cord. For example, transplantation of neural stem cells and bone marrow stromal cells actively promotes neuronal regeneration in animal models. These studies suggest that favorable host-cell microenvironment within the injury sites can be exploited for developing new therapeutic protocols for SCI. Furthermore, the discovery of neural progenitor cells and their subsequent isolation and propagation, the possibility of replacing lost neurons and providing an appropriate cellular bridge for the axon regrowth is possible.

Furthermore, the art has realized that the growth and survival of implanted neural cells or tissues is improved if a matrix substrate or scaffold is provided. As a result, a variety of synthetic and natural biodegradable materials have been developed for neural tissue regeneration and reconstruction which provide a structural support for cell growth and a conduit for local delivery of therapeutic agents. The commonly used implant systems for such purposes include carrier scaffolds of synthetic polymer (such as PLLA, PGA, and Hydrogel), methylcellulose and alginate substrates. Implant systems and carrier scaffolds may further comprise purified matrix coatings or self-assembling peptide scaffolds (such as fibrin, collagen I, and laminin peptides). Carrier scaffolds of alginate hydrogel and fibronectin seeded with Schwann cells are known to support neuronal survival and regeneration. Although these biopolymer substrate systems induce neuronal growth and regeneration process they exhibit many structural and biological limitations (as discussed herein).

However, despite these encouraging developments, a practical treatment for SCI remains elusive primarily due to lack of well-defined biomatrix system for in vitro studies and in vivo use. The present disclosure describes the use of the Applicants' novel biologically active human biomatrix to provide an in vivo trophic milieu which will allow for efficient tissue repair, neuronal regeneration and functional recovery. Moreover, no suitable carrier scaffold model or matrix substrate is currently available that employs human biomatrix and mimics spinal cord injury biology and reconstruction.

Although, biopolymer-based implant systems promote neuronal growth and tissue regeneration process, they exhibit several structural and biological limitations. A comparison of the properties of the HuBiogel™ matrix as compared to currently available materials is provided in Table 3.

As a result of the unique composition and formulation of the HuBiogel™ biomatrix, it has resulting physical and biological properties that allow it to overcome the shortcomings of currently available systems. The advantages of the HuBiogel™ human biomatrix composition, include, but are not limited to: i) the physical properties of the HuBiogel™ formulation allow direct injection of the matrix into the injured sites; ii) the defined formulation of the HuBiogel™ matrix provides a host-cell milieu that is well defined and can be precisely controlled by the addition of desired compounds, such as growth factors; and iii) the unique HuBiogel™ formulation mimics the biology of the target tissue, allowing stimulation of the implanted cells. As a result of the novel physical and biological properties of the HuBiogel™ matrix, it greatly improves neural tissue regeneration and functional recovery following SCI.

While most cells grow and survive better if a physical substrate for adhesion is provided, inclusion of soluble growth factors further enhances cellular organization and differentiation during tissue growth and remodeling. A number of potent endogenous regulators that influence the survival and growth of neurons have been identified. For example, delivery of FGF, VEGF, IGF (insulin growth factor) and EGF (epidermal growth factor) to spinal injury sites has been shown to produce mitogenic, angiogenic and neurotrophic effects. Brain-derived neurotrophic factor (BDNF) is effective in reduced necrotic zone and supports neuronal survival after spinal cord hemisection in adult rats. Neurotrophin-3 (NT-3) enhances sprouting of corticospinal tract cells after spinal cord lesion. A glial cell-derived neurotrophic factor (GDNF) when incorporated in fibrin glue promotes dorsal root regeneration into spinal cord.

Several recent studies have used a combination of growth factors. In particular, a combination of EGF and bFGF (basic fibroblast growth factor) showed better functional recovery than either factor alone and IGF and EGF rescued motor neurons better than each individually. Although stimulation of axonal growth is observed with local delivery of growth factors, physiological problems with polymer-based delivery and poor bioavailability of the growth factors have limited their therapeutic potential in SCI studies. The use of HuBiogel™ will allow a constant physiologically relevant, bioactive matrix with advantageous physical properties, such as controllable sustained release of growth factors.

Since HuBiogel™ is a malleable biomatrix, its natural microenvironment and activity can be precisely controlled by enrichment with specific growth stimulatory compounds, such as growth factors and biopeptides. These growth stimulatory compounds may be released in a controlled manner over time, providing enhanced stimulation of neurogenesis. To examine the ability of the HuBiogel™ biomatrix to support neural cell growth, neurospheres were isolated as described herein and grown on a three-dimensional HuBiogel™ coated substrate, such as a disc, microbead or other surface. in the presence or absence of specific stimulatory compounds.

The HuBiogel™ three-dimensional structures that may be employed have been described above and are also described in the Methods section herein. In one embodiment for application to neurogenesis, the following three-dimensional HuBiogel™ system was used. A sterile lucite two-chamber system (0.2-0.5 ml), similar to our transwell chambers, is used to prepare various HuBiogel™ three-dimensional scaffold configurations (in one embodiment, HuBiogel™ is used at a concentration of 3-5 mg/ml). The HuBiogel™ matrix three-dimensional scaffold configurations will be fit into multiwell culture plates. Prior to injection at sites of SCI or implant studies, the three-dimensional scaffold configurations are conditioned with defined media, which may be enriched with varying concentration of growth factors of interest (5-50 ng/ml) or other growth stimulatory compounds and mixed with target cells ($1-2\times10^6$/ml) to induce controlled cell growth and differentiation (i.e. 2-3 day coculture). The target cells may be contained within the three-dimensional scaffold configuration or may be cultured on the top thereof. Furthermore, the three-dimensional scaffold configurations may be placed on top of a layer of HuBiogel™ biomatrix, with may contain additional growth stimulatory compounds. Finally, the HuBiogel™ three-dimensional scaffold configuration may comprise various growth stimulatory agents or other compounds of interest. The various embodiments of the HuBiogel™ three-dimensional scaffold configuration are selected based on the desired functional state of the target cells, in one embodiment neurospheres. For example, if undifferentiated target cell growth is desired, the cells are cultured in the presence of a HuBiogel™ three-dimensional scaffold configuration without added growth stimulatory compounds. If activated, mitogenic cell growth is desired, target cells may be cultured in the presence of a three-dimensional scaffold configuration with added growth stimulatory agents, either included in the HuBiogel™ matrix of in the defined media. A graphical representation of this system is provided in FIG. 2D. Tissue-specific biomatrix scaffolds and defined cellular environment can be generated using HuBiogel™ enriched with FGF, NGF and EGF or other growth stimulatory compounds (including any growth factor or other growth stimulatory agent currently known).

Figure 8:
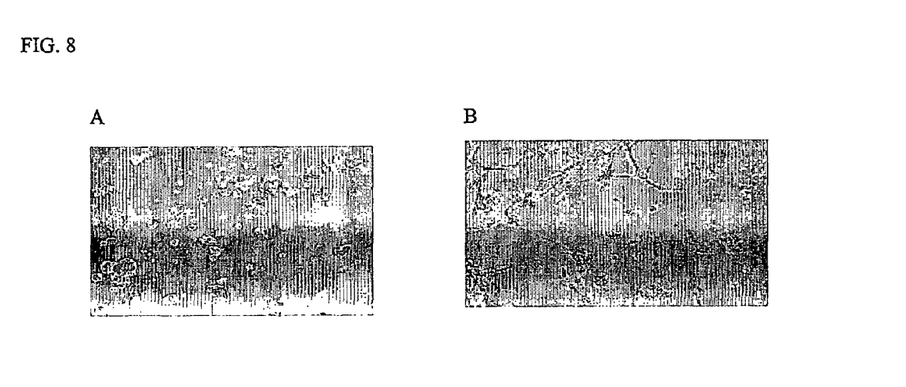
FIGS. 8A and 8B illustrate the promotion of neurogenesis by HuBiogel™ three-dimensional scaffold configurations. Neurospheres were isolated from adult rat brain as described and cultured on HuBiogel™ three-dimensional scaffold configurations (HuBiogel™ present a concentration of 3 mg/ml in the three-dimensional scaffold configurations) for seven days in the absence (FIG. 8A) or presence (FIG. 8B) of FGF and NGF (each present at 10 ng/ml, added to cell culture media).

In this example, neurospheres were isolated from adult rat brain as described and cultured on HuBiogel™ three-dimensional scaffold configurations (HuBiogel™ present a concentration of 3 mg/ml in the three-dimensional scaffold configurations) for seven days in the absence (FIG. 8A) or presence (FIG. 8B) of FGF and NGF (each present at 10 ng/ml and added to the cell culture medium). As shown in FIG. 8A, in the absence of growth stimulatory compounds, the HuBiogel™ three-dimensional scaffold configurations allowed active cellular growth (without differentiation) of the neurospheres. Neurosphere viability was maintained for at least 15 days. As shown in FIG. 8B, in the presence of growth stimulatory compounds, in this example NGF and EGF (10 ng/ml), the HuBiogel™ three-dimensional scaffold configurations supported growth factor-induced differentiation of the neurospheres. Interestingly, slow release of the growth stimulatory compounds, in this example growth factors, from the HuBiogel™ biomatrix paralleled the neurogenesis activity up to 15 days of coculture. In another study, similar neuron formation was observed when neurospheres were cocultured with HuBiogel™-seeded mesenchymal stem cells.

To further examine the ability of HuBiogel™ to support neurogenesis, tissue repair and functional recovery, HuBiogel™ three-dimensional scaffold configurations were evaluated in an established SCI model in adult rats. The SCI model system employed in these studies is described in the Methods section herein. Briefly, SCI is induced in the rats using a weight drop device as described by Noble and Wrathall. The procedure produces severe SCI in the rats in a reproducible and controllable manner. After inductions of SCI as described, Sprague-Dawley rats received an injection at the injury site of a HuBiogel™ three-dimensional matrix (15-20 μl of 3 mg/ml HuBiogel™) comprising $1 \times 10^6$ neural progenitor cells/derivatives (neurospheres) with or without growth stimulatory compounds two months after SCI. In this example, NGF and EGF were added to the HuBiogel™ three-dimensional matrix (25 ng/ml each). Other growth stimulators may be used in combination with the HuBiogel™ three-dimensional matrix as well; concentration ranges are typically from 5 to 50 ng/ml. HuBiogel™-treated animals demonstrated improved function and the injury site appeared significantly different from untreated animals.

HuBiogel™ treated animals also displayed superior behavioral responses as compared to control animals receiving no HuBiogel™ treatment after induced SCI. BBS scores were determined for control animals (no HuBiogel™ treatment) and treated animals (receiving HuBiogel™ treatment) as detailed in the Methods section below. BBS scores were determined for both groups at 2 weeks after induction of SCI and at 16-21 weeks after induction of SCI (corresponding to 8-13 weeks after HuBiogel™ treatment was initiated in the treatment group). The mean BBB pre-scores for the control group 2 weeks after SCI induction (6.8) were not significantly different from the mean scores of the control group 16-21 weeks after SCI induction (6.5). The mean BBB pre-scores for the treatment group 2 weeks after SCI induction (6.5) (prior to HuBiogel™ treatment) was similar to mean BBS pre-scores for the control group, indicating the extent of the SCI was equivalent However, the mean BBS pre-scores for the treatment group 16-21 weeks after SCI induction (7.5), or 8-13 weeks following HuBiogel™ treatment, were statistically significantly different from the mean BBS pre-scores obtained from the control group 2 weeks after SCI induction (6.5) (t-test, p=0.012). This indicates that HuBiogel™ treatment was capable of supporting neurogenesis, tissue repair and functional recovery.

Figure 9:
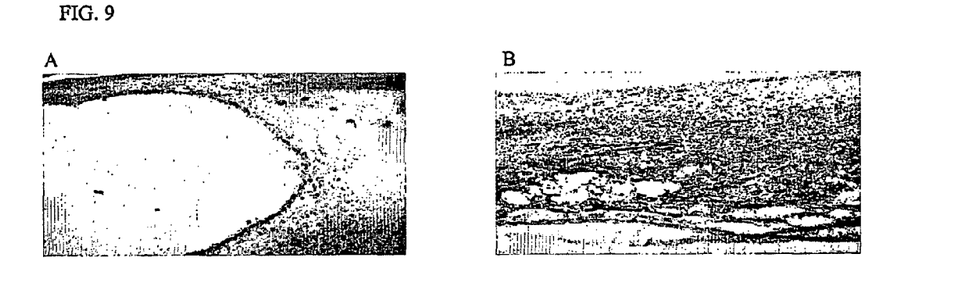

Histochemical analysis of SCI tissues from control group and treatment group animals were also performed (FIGS. 9A and 9B). FIGS. 9A and 9B show a low power view (10× objective) of longitudinal cut Niss1-stained sections of neural tissue at the site of SCI showing untreated control group animals (FIG. 9A) and animals from the treatment group 3 months after treatment with HuBiogel™ comprising neurospheres (FIG. 9B). The injury site of an untreated rat with a severe SCI shows one or more large cystic cavities surrounded by a thin rim of white matter. The white matter inhibitory glial scar. In the tissue section from a rat from the treatment group, the slide shows typical neural cell morphology comprising numerous small cavities with numerous trabeculae.

Immunohistochemical studies of SCI tissues from treatment group animals 3 months after treatment with HuBiogel™ comprising neurospheres were also performed (FIGS. 10A-C). FIGS. 10A-C show photomicrographs (25× objective) of the neural tissue at the site of SCI spinal cord injury site. In FIG. 10A, the type I collagen (the major component of HuBiogel™) organization is revealed by immunohistochemistry using anti-collagen I antibody and a rhodamine labeled secondary antibody. FIG. 10C shows the distribution of implanted cells (the implanted cells were labeled with CFDA-SE Cell Tracker kit, Molecular Probes, prior to implantation). A large number of cells are viable 3 months after implantation in the presence of HuBiogel™. In FIG. 10C shows the fused image showing the relationship of the labeled, implanted cells and the collagen I biomatrix architecture at the site of SCI. As can be seen, the viable implanted cells and the collagen I matrix co-localize, indicating the HuBiogel™ matrix is capable of supporting the growth of neurospheres in the SCI model. This suggests that the HuBiogel™ biomatrix will be successful in other in vivo applications as well. Low level background staining is noted in untreated tissue sections.

The practical application of HuBiogel™ scaffolds and implants extend beyond its application to neurogenesis and the other applications described herein as described herein. Additional uses include treatment of head and neck injury, burns, joint and bone reconstruction, plastic surgery and vascular surgeries. In general, the HuBiogel™ biomatrix has wide application in the field of reparative medicine since it is capable of maintaining and promoting the growth of a variety of cell types (both with and without active mitogenic growth or differentiation) and can be supplied in a variety of shapes and sizes for various uses. Furthermore, HuBiogel™ can custom formulated to provide growth stimulation, differentiation signals or other physiological cues to a desired cell type or system.

Growth and Additional Cell Types on Three-Dimensional HuBiogel™ Matrix

Figure 11:
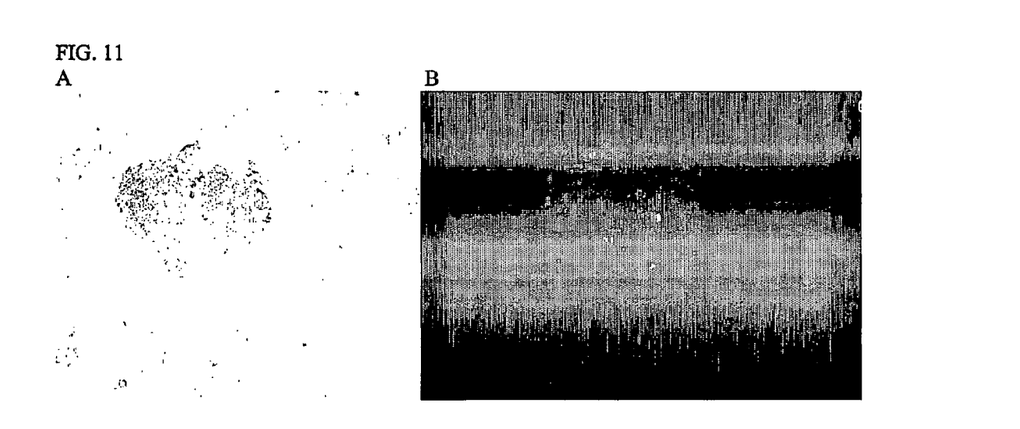
Figure 12A:
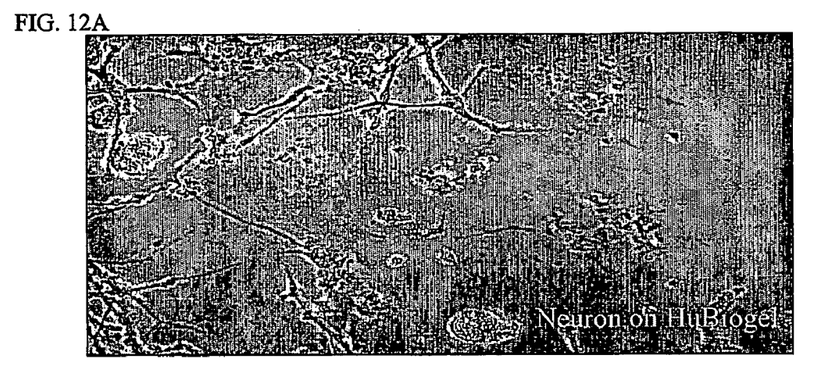
FIGS. 12A and 12B show MSC cells cultured on HuBiogel™ in the presence (FIG. 12B) and absence of NGF (FIG. 12A).
Figure 12B:
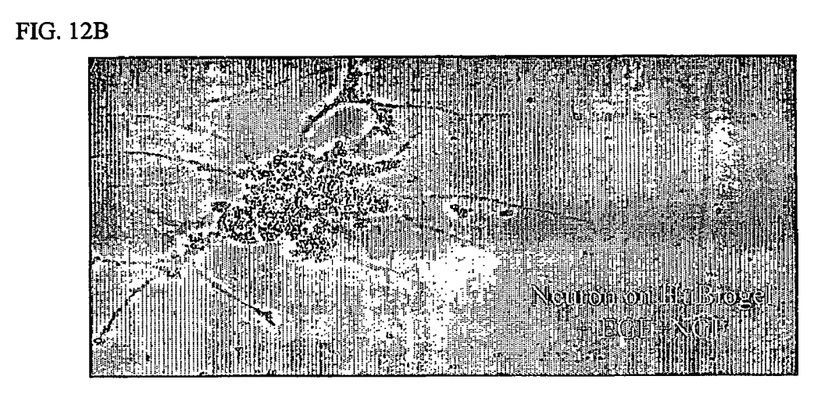
Figure 13:
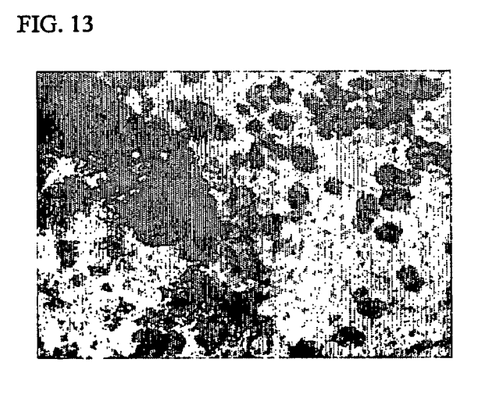
FIG. 13 shows liver cells cultured on HuBiogel™.

Other cell type may also be grown on HuBiogel™ matrices, with the above being exemplary in nature only. Theses other cell types include neurons, hepatocytes, sertoli cells and the like. For Example, FIGS. 11A and B show glioma cells cultured on HuBiogel™ containing matrices. FIG. 11A shows a light microscopy image, while FIG. 11B shows an image captured using FITC microscopy. FIGS. 12A and B show mesenchymal stem cells (MSC) cells cultured on HuBiogel™ in the presence (FIG. 12B) and absence of 15 ng/ml NGF (FIG. 12A). As can be seen, neuronal differentiation occurred only in the presence of NGF. FIG. 13 shows the growth of liver cells on the HuBiogel™ containing matrices.

Methods

Adult Stem Cell Isolation

Stem cells and/or progenitor cells are multipotent or totipotent cell types that have the capacity to self-renew, to proliferate in an undifferentiated state, and give rise to all the cell types of a particular tissue (mutlipotent) or all the cell types of an organism (totipotent). Standard preparation and isolation protocols of neural progenitor cells (neurospheres) from rat brain tissues are described in detail in the art. A variety of procedures may be used to isolate neural stem cells suitable for use in the instant disclosure. In one embodiment, the protocols described by Dr. Perduzi are employed (Woerly, et al., J. Neurosci. Research, 66, 1187 (2000); Woerley et al., Neurosurg Rev., 23, 59, (2000); Peduzzi, et al., J. Neurotrauma 18: 1146 (2001)). In brief, rat cortex are dissected out and minced tissue is washed and incubated in 0.05% Trypsin-0.5nM EDTA for 10 minutes. The cell pellet is resuspended in DMEM with 10% FCS (fetal calf serum), filtered through a 74 mm mesh and incubated overnight in DMEM with 10% FCS at 37° C., 5% $CO_2$. The isolated cells may be enriched for stem cells (Nestin-Ab positive cells selected using FACS) if desired. Cells will be grown as undifferentiated, activated or differentiated neurospheres (using the techniques described herein) at 37° C. and 5% $CO_2$. For undifferentiated, activated or differentiated neurospheres, the cells will be maintained in a defined serum-free media, DMEM/F12 (1:1, containing 15 nM HEPES buffer, sodium bicarbonate and L-glutamine) with insulin (20 mg/ml) and with/without specific growth factors (5-50 ng/ml) depending on the desired functional state of the neuroshperes. Immediately before treatment, cells may be labeled using CFDA-SE Cell Tracker kit (Molecular Probes) if it is desired to study the cells via immunohistochemistry after implantation.

Maintenance and Propagation of Stem Cells

Stem cell progenitors and their derivatives (neurospheres) alone produced some functional improvement in rats with the acute or sub-acute SCI, but not in the chronically injured rats. It is likely that the formation of cystic cavities lined by an inhibitory glial scar provides an inhospitable environment for the cellular growth. We believe that a well-defined 3D scaffold (HuBiogel™) that exhibits controlled biomatrix organization and encourages cellular growth may circumvent these problems and allow for reconstruction of neuronal tissue. To test this proposition, we will prepare specific GF-activated and/or differentiated stem cell populations within HuBiogel™ cocultures (see table above). These 3D cell-matrix scaffolds will be maintained for 1-2 days in defined media prior to SCI implantation studies. In some studies, if needed, cells can be treated in culture with media containing EGF and/or retinoic acid to encourage differentiation. In addition to neurosphere model, enriched stem cells (Nestin-Ab selected) are also available to us for extended validation studies.

Surgical Procedure

Sprague-Dawley rats (200-250 g) are given 0.25 ml/kg Ketalar (100 mg/ml) IM. After anesthetization with Halothane, the back of the animal will be shaved, ointment is applied to eyes to prevent drying and bladder is expressed. The animal is then placed on water circulating heating pad covered with a sterile towel during the surgery. After surgically exposing the spinal column at the lower thoracic level, a laminectomy will be performed at T8. An area of 2.6 mm will be exposed on the surface of the spinal cord. The dura will be left intact. The thoracic cavity is suspended using non-traumatic Ellis clamps on the spinous processes of T6 and T10. All animals will receive a severe spinal cord injury using a weight-drop device as described by Noble & Wrathall (Noble et al., Exp Neurol., 95, 530 (1987)). The impounder of the weight drop device will be carefully lowered to the surface of the spinal cord and the weight is dropped exactly 7.5 cm to create a severe SCI. A small piece of gel film will be it will be placed over the lesion site. The muscle tissue will be closed with absorbable suture and the skin will be closed with wound clips. During the surgery, breathing rate and pain response of the animal is closely monitored. Supplemental anesthesia is given if any response to pain is noted. Also during surgery, notes are kept on each animal.

Post surgery, the animal is monitored until alert (within 10 min), and then is monitored every 30 minutes for the next 3-4 hours. If the animal appears to be in pain, Buprenex is given (0.01 ml/kg). After the initial recovery period, animals are returned to the animal care facility. Post-operative rats are caged singly. Bladder is expressed manually at least 4 times daily until bladder reflexes return in the 7-14 days following the lesion.

SCI Study Design and Behavioral Testing

All animals receiving SCI as described will be behaviorally tested each week using BBB tests (Basso, et al., J. Neurotrauma 12, 1 (1995)) before and after treatment. At 1-2 months following injury, animals were randomly assigned to receive HuBiogel™ three dimensional scaffold preparations comprising progenitor cell formulation (wither with or without addition growth stimulatory agents) or serve as un-operated injured controls.

BBB locomotor test/score is a way of carefully evaluating the movements of the rats on a 21 point rating scale. Animals are evaluated in an open field area for 4 minutes. This test is based on the normal recovery seen after a mild spinal cord injury. It involves detailed analyses of movement including degree of motion at particular joints, stability of trunk during movement, weight bearing capabilities and paw placement during locomotion.

The inclined Plane test (Rivlin et al., J. of Neurosurgery. 47, 577 (1977)) is also used. The animal is placed head up on an adjustable inclined plane that is covered by a rubber mat. The plane angle is increased until the animal cannot maintain its position for 5 seconds. Normal rats can remain on the plane at an angle of 45°.

HuBiogel™ Three-Dimensional Scaffold and Stem Cell Transplant

The neural progenitor cells (as isolated above) are cocultured either in HuBiogel™ three-dimensional scaffold preparations (2-5 day) or embedded in defined biomatrix (both either growth stimulatory compound-free or growth stimulatory compound-enriched) formulations for direct injection or implantation at the site of SCI. Defined HuBiogel™ three-dimensional scaffold preparations with neural progenitor cells are prepared as described and kept on ice prior to implantation. At 1-2 months after SCI, the rats are treated with a formulation of HuBiogel™ containing neural progenitor cells (either with or without growth stimulants (10 rats/group). Each animal in the treatment group receives $1 \times 10^6$ cells. Neural progenitor stem cells are labeled with CFDA SE Cell Tracer kit (Molecular Probes) to identify the transplanted cells and aid in double labeling experiments. A fine gauge syringe stabilized using a stereotaxic frame is used to deliver the semi-gel HuBiogel™ three-dimensional scaffold preparations.

Histological Examination of Tissue

Deeply anesthetized rats are perfused through the heart with saline followed by 4% paraformaldehyde. The injury site is then either sectioned on a cryostat after cryoprotection with 30% sucrose or embedded in paraffin and sectioned on a cryostat. Immunohistochemistry is performed using standard protocols with standard antibodies to desired markers and proteins. In some cases, the stem cell derivatives are visualized using dual fluorescent microscope and immunochemistry analysis.

Statistical Data Analysis

Arithmetic means, standard deviation and Student's t-test for data significance are calculated by conventional formulas aided by computer software programs (e.g. Statview, Anova) as per our previous publications. P values>5% are considered statistically significant. Functional effects, cellular activation, biomarker profile, induction rates and dose-time dependence data sets will be compared.

All references to articles, books, patents, websites and other publications in this disclosure are considered incorporated by reference. The appended claim is added for purposes of claiming foreign priority only.

REFERENCES

Siegal G P, Wang M H, Rinehart C A, Goodly L J, Miller Y, Kaufman D G and Singh R K: Development of a human reconstituted basement membrane matrix for quantitation of the invasiveness of human cells. *Cancer Letters,* 69: 123-132, 1993.

Goodly L J, Singh R K, Wang M H and Siegal G P: In vivo modulation of human tumor cell growth by normal human extracellular matrix. *Tumor Biology,* 15:326-336, 1994

Singh R K and Siegal G P: Amino acid transport systems modulate human tumor cell growth and invasion: A working hypothesis. *Medical Hypothesis,* 44: 195-201, 1995.

Singh R K, Hardy R W, Wang M H, McDonald J M, Gladson C L and Siegal G P: Stearate inhibits human tumor cell invasion. *Invasion & Metastasis,* 15: 144-155, 1995

Xie H, Wang M H, Turner T, Singh R K, Siegal G P and Wells A: In vitro invasiveness of human prostate cells is modulated by EGFR-mediated signals. *Clin Exp Metastasis,* 13: 407-19, 1995

Singh R K, Rinehart C A, Kim J P, Rinehart S T, Kaufman D G and Siegal G P: Tumor cell invasion of basement membrane is regulated by amino acids. *Cancer Investigation,* 14: 6-18, 1996.

Zhang M, Singh R K, Wang M H, Wells A and Siegal G P: EGF modulates cell attachment to hyaluronic acid through the cell surface CD44. *Clin Exp Metastasis.* 14: 268-76, 1996.

Schwartz G G, Wang M H, Singh R K and Siegal G P: Dihydroxyvitamin D inhibits the invasiveness of human prostate cancer cells. *Cancer Epidemiol Biomarkers Prevent* 6: 727-32, 1997

Zhang M, Singh R K, Wang M H, Wells A and Siegal G P: EGF induces CD44 gene expression through a novel regulatory element in mouse fibroblasts. *J Biol Chem,* 272: 14139-146, 1997.

Gopurala B, Siegal G P, Zhang M, Ananthan S and Singh R K: A novel synthetic peptide inhibits tumor invasion in human cell-matrix bioassays. *Proc Am Assoc Cancer Res,* 39: 44, 1998

Siegal G P, Goparula B, Zhang M and Singh R K: VEGF-inducible aaT systems in human endothelial cells: Potential role in angiogenesis. *FASEB J* 15: 49, 2001.

Siegal G P, Listinsly J, Listinsky C, Singh R K and Alapati V: CD44-associated a-fucose modulates human breast tumor invasion. *FASEB J suppl.* 15: 49, 200 1.

Singh R K, Collingsworth P, Alapati V, Chen X and Siegal G P: Multiple human cell-biomatrix models for tissue growth and differentiation studies. In Vitro Cell Develop Biol, 38:11 2002.

TABLE 1

Comparison of HuBiogel ™ vs. Matrigel

|  | HuBiogel ™[1] | Matrigel[2] |
|---|---|---|
| Total Protein (mg/ml) | 5-8 | 10-15 |
| Laminin | 260 +/− 24 | 810 |
| Collagen I | 478 +/− 32 | n.s. |
| Collagen IV | 312 +/− 18 | 450 |
| Entactin | 164 +/− 20 | 120 |
| Tenascin | 68 +/− 6 | n.s. |
| Fibronectin | 18 +/− 4 | n.s |
| Proteoglycans | 14 +/− 6 | 25 |
| EGF | None | 0.7 ng |
| TGF-B | None | 3 ng |
| bFGF | None | 0.2 pg |
| PDGF | None | 12 pg |
| VEGF | None | 16 ng |
| Collagenases | None | detectable |

[1]mean concentration from 3-4 mini-preps
[2]from Becton-Dickinson Company data
n.s.—not stated, but assumed to be near zero

TABLE 2

Comparison of the Physical Properties of Various Biomatrix Systems

| Properties | HuBiogel ™ | Matrigel | Col./Fib. gels |
|---|---|---|---|
| Source/origin: | Human placenta (amnions) | Mouse EHS-tumor | Rat or mouse tissue |
| Physical form: | Semi-gel, Natural ECM | Liquid & gel Reconstituted ECM | Liquid & gel purified ECM |
| Gelation/Coating: | Uniform, flexible | Uneven or leaky | Uneven or leaky |
| Handling: | Stable gel (4° C. to 37° C.) | Temperature-sensitive | Temperature-sensitive |
| ECM-environment: | Defined, Physiological | Tumorigenic and Angiogenic | Artificial |
| Major ECM components: | Collagens I & IV, laminin, tenascin, entactin fibronectin, proteoglycans | Laminin collagen IV, entactin, proteoglycans | Native or denatured ECM proteins |
| Growth factors: | None, undetectable | TGF, EGF, PDGF, IGF, FGF | — |
| Proteases: | None, undetectable | Collagenase activity | — |
| Functional | Normal cell growth, | Uncontrolled | Requires induction or |

TABLE 2-continued

Comparison of the Physical Properties of Various Biomatrix Systems

| Properties | HuBiogel ™ | Matrigel | Col./Fib. gels |
|---|---|---|---|
| Advantages: | directed or controlled signaling milieu | cell activation, differentiation | other modifications |

TABLE 3

Comparsion of the Properties of Various Bioscaffold and Implant Systems

| | HuBiogel ™ system | Biopolymer system | Purified matrix system |
|---|---|---|---|
| Source/ Environment | Human, Physiological ECM composition | Synthetic grafts Artificial substrates | Animal-derived ECM proteins or peptides |
| Current system | Novel, well-defined biomatrix system | PLA, PLGA, Hydrogel, Neurogel | Fibrin, collagen I, alginate laminin proteins |
| Structural properties | Semi-gel and Injectable formulation | Solid implants, Non-injectable | Gel implants, Non-injectable |
| Biological properties | Controlled cell growth, differentiation & organization | Requires growth channels, Poor biocompability & uncontrolled milieu | Thrombogenic or scarring effects, Poor cell survival & organization |

What is claimed:

1. An isolated biomatrix composition comprising collagen I, collagen IV, laminin, entactin, and tenascin, wherein collagen I is present in a concentration greater than a concentration of collagen IV, laminin, entactin and tenascin, said composition is derived from a human basement membrane tissue and said composition is essentially free of endogenous collagenase.

2. The composition of claim 1 where the two most abundant components are collagen I and collagen IV, each of said collagen I and collagen IV being present in a concentration greater than a concentration of laminin, entactin, or tenascin.

3. The composition of claim 1 where the collagen I is present in a range of 35-46% by weight, collagen IV is present in a range of 19-33% by weight, laminin is present in a range of 16-21% by weight, entactin is present in a range of 7.5 to 14.5% by weight, and tenascin is present in a range of 3.5-7.0% by weight.

4. The composition of claim 1 where the collagen I is present at a concentration of 36% by weight, collagen IV is present at a concentration 24% by weight, laminin is present at a concentration 20% by weight, entactin is present at a concentration of 12.5% by weight, and tenascin is present at a concentration 5% by weight.

5. The composition of claim 1 where said composition is derived from a human placental amnion.

6. The composition of claim 1 where the composition is essentially free of endogenous growth stimulants and proteolytic enzymes.

7. The composition of claim 6 where the growth stimulants are selected from the group consisting of EGF, NGF, FGF, bFGF, VEGF, HGF, BDNF, and GDNF.

8. The composition of claim 1 where said composition is capable of sustaining the viability of a non-transformed target cell type by providing a suitable environment for said non-transformed target cell type without inducing differentiation of said non-transformed target cell type.

9. The composition of claim 8 where the non-transformed target cell type is selected from the group consisting of: epithelial cells, stem cells, endothelial cells, transgenic cells, liver cells and neural cells.

10. The composition of claim 9 where the stem cells are totipotent or pluripotent.

11. The composition of claim 1 where said composition is capable of supporting the controlled growth of transformed cell types.

12. The composition of claim 1 where said composition is used for the study of physiological and pathological processes by culturing a population of target cells relevant to said physiological or pathological processes on the composition of claim 1 and observing at least one characteristic relevant to said physiological process of said target cell culture over time.

13. The composition of claim 12 where the physiological processes are selected from the group consisting of: tissue growth, tissue development, bone remodeling, wound healing, angiogenesis, reproduction, and aging.

14. The composition of claim 12 where the pathological processes are selected from the group consisting of tumorigenesis, metastasis, angiogenesis, vascular dysfunction, arthritis and atherosclerosis.

15. The composition of claim 1 where said composition forms a gel over a temperature range of 4 degrees C. to 37 degrees C.

* * * * *